US009169350B2

(12) United States Patent
Shen

(10) Patent No.: US 9,169,350 B2
(45) Date of Patent: *Oct. 27, 2015

(54) N-MALEIMIDYL POLYMER DERIVATIVES

(71) Applicant: Nektar Therapeutics, San Francisco, CA (US)

(72) Inventor: Xiaoming Shen, Millbrae, CA (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/627,917

(22) Filed: Feb. 20, 2015

(65) Prior Publication Data

US 2015/0166725 A1  Jun. 18, 2015

Related U.S. Application Data

(63) Continuation of application No. 14/283,788, filed on May 21, 2014, which is a continuation of application No. 13/890,799, filed on May 9, 2013, now Pat. No. 8,765,111, which is a continuation of application No. 11/134,076, filed on May 20, 2005, now Pat. No. 8,454,946, which is a continuation of application No. 10/408,834, filed on Apr. 7, 2003, now Pat. No. 6,911,197, which is a continuation of application No. 09/790,250, filed on Feb. 21, 2001, now Pat. No. 6,602,498.

(60) Provisional application No. 60/183,833, filed on Feb. 22, 2000.

(51) Int. Cl.
| *A61K 31/74* | (2006.01) |
| *C08G 65/333* | (2006.01) |
| *A61K 47/48* | (2006.01) |
| *C08G 65/48* | (2006.01) |
| *C08G 65/00* | (2006.01) |

(52) U.S. Cl.
CPC .......... *C08G 65/33337* (2013.01); *A61K 31/74* (2013.01); *A61K 47/48176* (2013.01); *A61K 47/48215* (2013.01); *A61K 47/48338* (2013.01); *C08G 65/00* (2013.01); *C08G 65/33396* (2013.01); *C08G 65/48* (2013.01)

(58) Field of Classification Search
CPC ............ A61K 31/74; A61K 47/48176; A61K 47/48215; A61K 47/48338; C08G 65/33396; C08G 65/00; C08G 65/48
See application file for complete search history.

(56) References Cited

U.S. PATENT DOCUMENTS

| 4,179,337 | A | 12/1979 | Davis et al. |
| 4,675,414 | A | 6/1987 | DeFusco et al. |
| 4,761,460 | A | 8/1988 | Otsuka et al. |
| 4,775,729 | A | 10/1988 | DeFusco et al. |
| 5,166,322 | A | 11/1992 | Shaw et al. |
| 5,585,484 | A | 12/1996 | Acharya et al. |
| 5,990,237 | A | 11/1999 | Bentley et al. |
| 6,303,119 | B1 | 10/2001 | Weisgerber et al. |
| 6,348,558 | B1 | 2/2002 | Harris et al. |
| 6,495,659 | B2 * | 12/2002 | Bentley et al. ............... 528/425 |
| 6,602,498 | B2 * | 8/2003 | Shen .......................... 424/78.08 |
| 6,737,505 | B2 * | 5/2004 | Bentley et al. ............... 528/425 |
| 6,911,197 | B2 * | 6/2005 | Shen .......................... 424/78.08 |
| 8,454,946 | B2 * | 6/2013 | Shen .......................... 424/78.08 |
| 8,765,111 | B2 * | 7/2014 | Shen .......................... 424/78.08 |
| 2002/0082345 | A1 | 6/2002 | Kozlowski et al. |
| 2003/0162693 | A1 | 8/2003 | Winslow et al. |
| 2003/0170474 | A1 | 9/2003 | Qiao et al. |
| 2006/0013797 | A1 | 1/2006 | Shen |
| 2014/0256957 | A1 | 9/2014 | Shen |

FOREIGN PATENT DOCUMENTS

| DE | 19652544 | 6/1988 |
| EP | 0 149 520 | 7/1985 |
| EP | 0 251 110 | 1/1988 |
| EP | 0 318 162 | 5/1989 |
| JP | 08041195 | 2/1996 |
| WO | WO 92/16221 | 10/1992 |
| WO | WO 95/11987 | 5/1995 |
| WO | WO 95/34326 | 12/1995 |
| WO | WO 96/32841 | 10/1996 |
| WO | WO 98/30575 | 7/1998 |
| WO | WO 98/31383 | 7/1998 |
| WO | WO 99/03887 | 1/1999 |
| WO | WO 00/05582 | 2/2000 |
| WO | WO 00/62827 | 10/2000 |
| WO | WO 03/059363 | 7/2003 |

OTHER PUBLICATIONS

ACS Registry No. 146226-29-1, (1993).
ACS Registry No. 58914-60-6, (1976).
Alam, et al., "The importance of being knotted: effects of the C-terminal knot structure on enzymatic and mechanical properties of bovine carbonic anhydrase II", FEBS Letters, vol. 519, pp. 35-40, (2002).
Blessing, et al., "Different Strategies for Formation of PEGylated EGF-Conjugated PEI/DNA Complexes for Targeted Gene Delivery", Bioconjugate Chem., vol. 12, pp. 529-537, (2001).
Casey, et al., "Improved Tumour Targeting of di-Fab' Fragments Modified with Polyethylene Glycol", Tumor Targeting, pp. 235-244, (2000).
Christakopoulos, et al., "Enhancement of pH-stability of a low molecular mass endoglucanase from *Fusarium oxysporum* by protein pegylation", Carbohydrate Research, vol. 314, pp. 95-99, (1998).

(Continued)

*Primary Examiner* — Blessing M Fubara
(74) *Attorney, Agent, or Firm* — Mark A. Wilson

(57) ABSTRACT

The invention is directed to multi-functional N-maleimidyl polymer derivatives comprising a water soluble and non-peptidic polymer backbone having a terminal carbon, such as a poly(alkylene glycol), the terminal carbon of the polymer backbone being directly bonded to the nitrogen atom of a N-maleimidyl moiety without a linking group therebetween. The invention also provides two methods of preparing such linkerless N-maleimidyl polymer derivatives.

1 Claim, No Drawings

(56) References Cited

OTHER PUBLICATIONS

Dauty, et al., "Intracellular Delivery of Nanometric DNA Particles via the Folate Receptor", Bioconjugate Chem., vol. 13, pp. 831-839, (2002).
Frisch, et al., "Synthesis of Short Polyoxyethylene-Based Heterobifunctional Cross-Linking Reagents. Application to the Coupling of Peptides to Liposomes", Bioconjugate Chem., vol. 7, pp. 180-186, (1996).
Goodson, et al., "Site-Directed Pegylation of Recombinant Interleukin-2 at its Glycosylation Site", Bio/Technology, vol. 8, pp. 343-346, (1990).
He, et al., "Reducing the Immunogenicity and Improving the in Vivo Activity of Trichosanthin by Site-Directed Pegylation", Life Sciences, vol. 65, No. 4, pp. 355-368, (1999).
Hill, et al., "Diels-Alder Bioconjugation of Diene-Modified Oligonucleotides", J. Org. Chem., vol. 66, pp. 5352-5358, (2001).
Juszczak, et al., "UV Resonance Raman Study of β93-Modified Hemoglobin A: Chemical Modifier-Specific Effects and Added influences of Attached Poly(ethylene glycol) Chains", Biochemistry, vol. 41, pp. 376-385, (2002).
Keller, et al., "Preparation and Some Properties of Maleimido Acids and Maleoyl Derivatives of Peptides", Helvetica Chimica Acta, vol. 58, pp. 531-540, (1975).
Kogan, "The Synthesis of Substituted Methoxy-Poly(EthyleneGlycol) Derivatives Suitable for Selective Protein Modification", Synthetic Communications, vol. 22, No. 16, pp. 2417-2424, (1992).
Kuehne, et al., "Synthesis and Characterization of Membrane-Active GALA-OKT9 Conjugates", Bioconjugate Chem., vol. 12, pp. 742-749, (2001).
Lee, et al., "A new gene delivery formulation of polyethylenimine/DNA complexes coated with PEG conjugated fusogenic peptide", Journal of Controlled Release, vol. 76, pp. 183-192, (2001).
Lee, et al., "Syntheses and Biological Activities of N-Alaninylmaleimide and its Polymers", J.M.S. Pure Appl. Chem A34(1), pp. 1-11, (1997).
Makmura, et al., "Development of a Sensitive Assay to Detect Reversibly Oxidized Protein Cysteine Sulfhydryl Groups", Antioxidants & Redox Signaling, vol. 3, No. 6, pp. 1105-1118, (2001).
Mao, et al., "Chitosan-DNA nanoparticles as gene carriers: synthesis, characterization and transfection efficiency", Journal of Controlled Release, vol. 70, pp. 399-421, (2001).
Marshall, "The Synthesis of Substituted Methoxy-Poly(ethyleneglycol) Derivatives Suitable for Selective Protein Modification", Synthetic Communications, vol. 22, No. 16, pp. 2417-2424, (1992).
Mehta, et al., "Maleamic and Citraconamic Acids, Methyl Esters, and Imides", J. Org. Chem., vol. 25, pp. 1012-1015, (Jun. 1960).
Olivier, et al., "Synthesis of Pegylated Immunonanoparticles", Pharmaceutical Research, vol. 19, No. 8, pp. 1137-1143, (2002).
Romani, et al., "Synthesis of Unsymmetrical Cystine Peptide: Directed Disulfide Pairing with the Sulfenohydrazide Method", Chem. Peptides and Proteins, vol. 2, pp. 29-34, (1984).
Schmidt, et al., "Force Tolerances of Hybrid Nanodevices", Nano Letters, vol. 2, No. 11, pp. 1229-1233, (2002).
Tang, et al., "Preparation of a New PEGylation Reagent for Sulfhydryl-containing Polypeptide", Tetrahedron Letters, vol. 35, No. 35, pp. 6515-6516, (1994).
Tsutsumi, et al., "Site-specific chemical modification with polyethylene glycol of recombinant immunotoxin anti-Tac(Fv)-PE38 (LMB-2) improves antitumor activity and reduces animal toxicity and immunngenicity", PNAS, vol. 97, No. 15, pp. 8548-8553, (2000).
Vargas, et al., "Diels-Alder Modification of Poly(ethylene terephthalate-co-anthracene-2,6-carboxylate) with N-Substituted Maleimides", J. Polymer Sci. Part A: Polymer Chem., vol. 40, pp. 3256-3263, (2002).
Walker, "The Mitsunobu Reaction: A Novel Method for the Synthesis of Bifunctional Maleimide Linkers", Tetrahedron Letters, vol. 35, No. 5, pp. 665-668, (1994).
Wu, et al., "p53 protein oxidation in cultured cells in response to pyrrolidine dithiocarbamate: a novel method for relating the amount of p53 oxidation in vivo to the regulation of p53-responsive genes", Biochem. J., vol. 351, pp. 87-93, (2000).
Shearwater Polymers, Inc., Polyethylene Glycol Derivatives, 55 pages, Catalog 1997-1998, (Jul. 1997).
PCT Notification of Transmittal of the International Search Report or the Declaration, corresponding to PCT Application No. PCT/US2001/005528 mailed Sep. 13, 2001.
PCT Written Opinion corresponding to PCT Application No. PCT/US2001/005528 mailed Apr. 25, 2002.
PCT Notification of Transmittal of the International Preliminary Examination Report corresponding to PCT Application No. PCT/US2001/005528 mailed Jul. 2, 2002.
Shearwater Polymers, Inc., Polyethylene Glycol Derivatives, 50 pages, Catalog—(Mar. 1995).
Shearwater Polymers, Inc., Polyethylene Glycol and Derivatives: Functionalized Biocompatible Polymers for Research and Pharmaceuticals, 50 pages, Catalog—(Jan. 2000).

* cited by examiner

N-MALEIMIDYL POLYMER DERIVATIVES

CROSS-REFERENCE TO RELATED APPLICATIONS

This application is a continuation of U.S. patent application Ser. No. 14/283,788, filed May 21, 2014, now U.S. Pat. No. 8,992,902, which is a continuation of U.S. patent application Ser. No. 13/890,799, filed May 9, 2013, now U.S. Pat. No. 8,765,111, which is a continuation of U.S. patent application Ser. No. 11/134,076, filed May 20, 2005, now U.S. Pat. No. 8,454,946, which is a continuation of U.S. patent application Ser. No. 10/408,834, filed Apr. 7, 2003, now U.S. Pat. No. 6,911,197, which is a continuation of U.S. patent application Ser. No. 09/790,250, filed Feb. 21, 2001, now U.S. Pat. No. 6,602,498, which claims the benefit of priority to U.S. Provisional Patent Application Ser. No. 60/183,833, filed on Feb. 22, 2000, all of which are incorporated herein by reference in their entireties.

FIELD OF THE INVENTION

This invention relates to N-maleimidyl derivatives of water-soluble and non-peptidic polymers.

BACKGROUND OF THE INVENTION

Covalent attachment of the hydrophilic polymer poly(ethylene glycol), abbreviated PEG, also known as poly(ethylene oxide), abbreviated PEO, to molecules and surfaces is of considerable utility in biotechnology and medicine. In its most common form, PEG is a linear polymer terminated at each end with hydroxyl groups:

HO—$CH_2CH_2$O—($CH_2CH_2$O)$_n$—$CH_2CH_2$—OH

The above polymer, alpha-,omega-dihydroxylpoly(ethylene glycol), can be represented in brief form as HO—PEG—OH where it is understood that the —PEG— symbol represents the following structural unit:

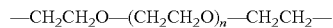

—$CH_2CH_2$O—($CH_2CH_2$O)$_n$—$CH_2CH_2$— where n typically ranges from about 3 to about 4000.

PEG is commonly used as methoxy-PEG—OH, or mPEG in brief, in which one terminus is the relatively inert methoxy group, while the other terminus is a hydroxyl group that is subject to ready chemical modification. The structure of mPEG is given below.

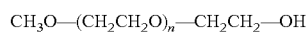

$CH_3$O—($CH_2CH_2$O)$_n$—$CH_2CH_2$—OH

Random or block copolymers of ethylene oxide and propylene oxide, shown below, are closely related to PEG in their chemistry, and they can be substituted for PEG in many of its applications.

HO—$CH_2$CHRO($CH_2$CHRO)$_n$$CH_2$CHR—OH wherein each R is independently H or $CH_3$.

PEG is a polymer having the properties of solubility in water and in many organic solvents, lack of toxicity, and lack of immunogenicity. One use of PEG is to covalently attach the polymer to insoluble molecules to make the resulting PEG-molecule "conjugate" soluble. For example, it has been shown that the water-insoluble drug paclitaxel, when coupled to PEG, becomes water-soluble. Greenwald, et al, *J. Org Chem.*, 60:331-336 (1995).

To couple PEG to a molecule, such as a protein, it is often necessary to "activate" the PEG by preparing a derivative of the PEG having a functional group of terminus thereof. The functional group is chosen based on the type of available reactive group on the molecule that will be coupled to the PEG. For example, the functional group could be chosen to react with an amino group on a protein in order to form a PEG-protein conjugate. There is a continuing need in the art for new activated PEG derivatives useful for coupling to biologically active molecules.

SUMMARY OF THE INVENTION

The invention provides multi-functional N-maleimidyl polymer derivatives, such as bifunctional and multi-arm N-maleimidyl PEG derivatives, and methods for preparing such derivatives. The derivatives of the invention have no linking group between the terminus of the polymer backbone and the nitrogen atom of the maleimidyl moiety. The absence of a linker minimizes structural complexity of the derivative and simplifies synthesis of the derivative. Further, the "linkerless" derivatives of the invention typically cost less to produce and exhibit reduced likelihood of degradation in vivo. Such maleimidyl-activated polymers are suitable for coupling to other molecules bearing thiol groups, including, but not limited to, proteins having one or more cysteine thiol groups.

The invention provides a multi-functional N-maleimidyl polymer derivative comprising a water soluble and non-peptidic polymer backbone having an average molecular weight from about 800 Da to about 100,000 Da, the polymer backbone having a first terminus bonded to a first functional group and a second terminus having a terminal carbon, wherein said terminal carbon of said second terminus is directly bonded to a N-maleimidyl moiety having the structure:

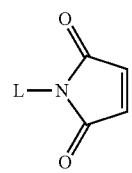

wherein L is the point of bonding to the terminal carbon of the second terminus of the polymer backbone. The second functional group may be a second maleimidyl moiety or any other functional group known in the art that will not react with a maleimidyl group. The polymer backbone has two or more termini "activated" with a functional group such as a maleimidyl group.

The polymer backbone is preferably a poly(alkylene glycol), copolymer thereof, terpolymer thereof, or mixture thereof. Examples include poly(ethylene glycol), poly(propylene glycol), and copolymers of ethylene glycol and propylene glycol. As explained in greater detail below, preferred embodiments of the invention utilize PEG polymers, such as bifunctional PEG, multiarmed PEG, forked PEG, branched PEG, pendent PEG, and PEG with degradable linkages therein.

The invention provides two methods of preparing the linkerless N-maleimidyl polymer derivatives. In one method, a water-soluble and non-peptidic polymer backbone having an average molecular weight from about 800 Da to about 100,000 Da, the polymer backbone having a first terminus bonded to a first functional group and a second terminus bonded to an amine group, is reacted with maleic anhydride to form an open ring intermediate. The open ring intermediate is heated in the presence of acetic anhydride and a salt of acetic acid, such as sodium or potassium acetate, to form a multi-functional N-maleimidyl polymer derivative product. In a second method, an N-alkoxycarbonylmaleimide is reacted with the water-soluble and non-peptidic polymer backbone having an average molecular weight of about 800 Da to about 100,000 Da and a terminal amine group to form the N-maleimidyl polymer derivative product in a single step. In one embodiment, the polymer backbone used in either reaction method is X—PEG—NH$_2$, wherein PEG is poly(ethylene glycol) and X is a second functional group.

Using either method, the N-maleimidyl polymer derivative product can be purified prior to use. For example, ion exchange chromatography and precipitation techniques can be employed to purify the final product. The N-maleimidyl polymer derivative product can be reacted with a biologically active agent to form a biologically active polymer conjugate. As noted above, the N-maleimidyl polymer derivatives are particularly suited for reaction with thiol groups, such as thiol groups on proteins or peptides.

DETAILED DESCRIPTION OF THE INVENTION

The terms "functional group", "active moiety", "activating group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules. The term "active", when used in conjunction with functional groups, is intended to include those functional groups that react readily with electrophilic or nucleophilic groups on other molecules, in contrast to those groups that require strong catalysts or highly impractical reaction conditions in order to react. For example, as would be understood in the art, the term "active ester" would include those esters that react readily with nucleophilic groups such as amines. Typically, an active ester will react with an amine in aqueous medium in a matter of minutes, whereas certain esters, such as methyl or ethyl esters, require a strong catalyst in order to react with a nucleophilic group. Due to its relatively inert nature, an alkoxy group is not considered a functional group herein.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pHs, e.g., under physiological conditions for an extended period of time, perhaps even indefinitely. Hydrolytically unstable or degradable linkages means that the linkages are degradable in water or in aqueous solutions, including for example, blood. Enzymatically unstable or degradable linkages means that the linkage can be degraded by one or more enzymes. As understood in the art, PEG and related polymers may include degradable linkages in the polymer backbone or in the linker groups between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include carbonate linkages; imine linkages resulted from reaction of an amine and an aldehyde (see, e.g., Ouchi et al., *Polymer Preprints*, 38(1): 582-3 (1997), which is incorporated herein by reference); phosphate ester linkages formed by reacting an alcohol with a phosphate group; hydrazone linkages which are reaction product of a hydrazide and an aldehyde; acetal linkages that are the reaction product of an aldehyde and alcohol; orthoester linkages that are the reaction product of a formate and an alcohol; peptide linkages formed by an amine group, e.g., at an end of a polymer such as PEG, and a carboxyl group of a peptide; and oligonucleotide linkages formed by a phosphoramidite group, e.g., at the end of a polymer, and a 5' hydroxyl group of an oligonucleotide.

The term "biologically active molecule", "biologically active moiety" or "biologically active agent" when used herein means any substance which can affect any physical or biochemical properties of a biological organism, including but not limited to viruses, bacteria, fungi, plants, animals, and humans. In particular, as used herein, biologically active molecules include any substance intended for diagnosis, cure mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

The terms "alky," "alkene," and "alkoxy" include straight chain and branched alkyl, alkene, and alkoxy, respectively. The term "lower alkyl" refers to C1-C6 alkyl. The term "alkoxy" refers to oxygen substituted alkyl, for example, of the formulas —OR or —ROR$^1$, wherein R and R$^1$ are each independently selected alkyl. The terms "substituted alkyl" and "substituted alkene" refer to alkyl and alkene, respectively, substituted with one or more non-interfering substituents, such as but not limited to, C3-C6 cycloalkyl, e.g., cyclopropyl, cyclobutyl, and the like; acetylene; cyano; alkoxy, e.g., methoxy, ethoxy, and the like; lower alkanoyloxy, e.g., acetoxy; hydroxy; carboxyl; amino; lower alkylamino, e.g., methylamino; ketone; halo, e.g., chloro or bromo; phenyl; substituted phenyl, and the like. The term "halogen" includes fluorine, chlorine, iodine and bromine.

"Aryl" means one or more aromatic rings, each of 5 or 6 carbon atoms. Multiple aryl rings may be fused, as in naphthyl or unfused, as in biphenyl. Aryl rings may also be fused or unfused with one or more cyclic hydrocarbon, heteroaryl, or heterocyclic rings.

"Substituted aryl" is aryl having one or more non-interfering groups as substituents.

"Non-interfering substituents" are those groups that yield stable compounds. Suitable non-interfering substituents or radicals include, but are not limited to halo, $C_1$-$C_{10}$ alkyl, $C_2$-$C_{10}$ alkenyl, $C_2$-$C_{10}$ alkynyl, $C_1$-$C_{10}$ alkoxy, $C_7$-$C_{12}$ aralkyl, $C_7$-$C_{12}$ alkaryl, $C_3$-$C_{10}$ cycloalkyl, $C_3$-$C_{10}$ cycloalkenyl, phenyl, substituted phenyl, toluoyl, xylenyl, biphenyl, $C_2$-$C_{12}$ alkoxyalkyl, $C_7$-$C_{12}$ alkoxyaryl, $C_7$-$C_{12}$ aryloxyalkyl, $C_6$-$C_{12}$ oxyaryl, $C_1$-$C_6$ alkylsulfinyl, $C_1$-$C_{10}$ alkylsulfonyl, —(CH$_2$)$_m$—O—($C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —NO$_2$, —CN, —NRC(O)—)$C_1$-$C_{10}$ alkyl), —C(O)—($C_1$-$C_{10}$ alkyl), $C_2$-$C_{10}$ thioalkyl, —C(O)O—($C_1$-$C_{10}$ alkyl), —OH, —SO$_2$, =S, —COOH, —NR$_2$, carbonyl, —C(O)—($C_1$-$C_{10}$ alkyl)—CF$_3$, —C(O)—CF$_3$, —C(O)NR$_2$, —($C_1$-$C_{10}$ alkyl)—S—($C_6$-$C_{12}$ aryl), —C(O)—($C_6$-$C_{12}$ aryl), —(CH$_2$)$_m$—O—(CH$_2$)$_m$—O—($C_m$—O—($_1$-$C_{10}$ alkyl) wherein each m is from 1 to 8, —C(O)NR$_2$, —C(S)NR$_2$, —SO$_2$NR$_2$, —SO$_2$NR$_2$, —NRC(O)NR$_2$, —NRC(S)NR$_2$, salts thereof, and the like. Each R as used herein is H, alkyl or substituted alkyl, aryl or substituted aryl, aralkyl, or alkaryl.

The invention provides a multi-functional N-maleimidyl polymer derivative comprising a water soluble and non-peptidic polymer backbone having an average molecular weight from about 800 Da to about 100,000 Da, the polymer backbone having a first terminus bonded to a first functional group and a second terminus having a terminal carbon, wherein said terminal carbon of said second terminus is directly bonded to a N-maleimidyl moiety having the structure:

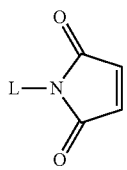

wherein L is the point of bonding to the terminal carbon of the second terminus of the polymer backbone.

The polymer backbone of the water-soluble and non-peptidic polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly(ethylene glycol) in any of its forms, including bifunctional PEG, multiarmed PEG, forked PEG, branched PEG, pendent PEG (i.e. PEG or related polymers having one or more functional groups pendent to the polymer backbone), or PEG with degradable linkages therein.

PEG is typically clear, colorless, odorless, soluble in water, stable to heat, inert to many chemical agents, does not hydrolyze or deteriorate, and is generally non-toxic. Poly(ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects. PEG having the formula —CH$_2$CH$_2$O—(CH$_2$CH$_2$O)$_n$—CH$_2$CH$_2$—, where n is from about 3 to about 4000, typically from about 20 to about 2000, is one useful polymer in the practice of the invention. PEG having a molecular weight of from about 800 Da to about 100,000 Da are particularly useful as the polymer backbone.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol oligomers, pentaerythritol and sorbitol. The central branch moiety can also be derived from several amino acids, such as lysine. The branched poly (ethylene glycol) can be represented in general faun as R(—PEG—OH)$_m$ in which R is derived from a core moiety, such as glycerol, glycerol oligomers, or pentaerythritol, and m represents the number of arms. Multi-armed PEG molecules, such as those described in U.S. Pat. No. 5,932,462, which is incorporated by reference herein in its entirety, can also be used as the polymer backbone.

Branched PEG can also be in the form of a forked PEG represented by PEG(—YCHZ$_2$)$_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown below, this hydrolysis results in cleavage of the polymer into fragments of lower molecular weight:

—PEG—CO$_2$—PEG—+H$_2$O→—PEG—CO$_2$H+ HO—PEG—

It is understood by those skilled in the art that the term poly(ethylene glycol) or PEG represents or includes all the above forms.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as polypropylene glycol) ("PPG"), copolymers thereof (e.g. copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da.

Those of ordinary skill in the art will recognize that the foregoing list for substantially water soluble and non-peptidic polymer backbones is by no means exhaustive and is merely illustrative, and that all polymeric materials having the qualities described above are contemplated.

The polymer derivatives of the invention are "multi-functional", meaning that the polymer backbone has at least two termini, and possibly as many as about 300 termini, functionalized or activated with a functional group. Multifunctional polymer derivatives include linear polymers having two termini, each terminus being bonded to a functional group which may be the same or different.

In one embodiment, the polymer derivative has the structure:

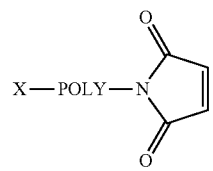

wherein:

POLY is a linear water soluble and non-peptidic polymer having a terminal carbon (e.g., PEG), the terminal carbon being directly bonded to the nitrogen atom of the N-maleimidyl moiety; and X is a second functional group.

Examples of suitable functional groups for use as X include hydroxyl, protected hydroxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate. The functional group is typically chosen for attachment to a functional group on a biologically active agent. As would be understood, the selected X moiety should be compatible with the maleimidyl group so that reaction with the maleimidyl group does not occur. Particularly preferred functional groups include —OH, —NH$_2$, —CO$_2$H, —CHO, —CH(OC$_2$H$_5$)$_2$, N-hydroxysuccinimidyl esters, 1-benzotriazolyl esters, N-hydroxysuccinimidyl carbonates, 1-benzotriazolyl carbonates, and tresylate. The N-maleimidyl polymer derivatives may be homobifunctional, meaning that the second functional group (i.e., X) is also N-maleimidyl moiety, or heterobifunctional, meaning that the second functional group is a different functional group.

As would be understood in the art, the term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the invention.

Specific examples of terminal functional groups in the literature include N-succinimidyl carbonate (see e.g., U.S. Pat. Nos. 5,281,698, 5,468,478), amine (see e.g., Buckmann et al. *Makromol. Chem.* 182:1379 (1981), Zalipsky et al. *Eur. Polym J.* 19:1177 (1983)), hydrazide (See e.g., Andresz et al. *Makromol. Chem.* 179:301 (1978)), succinimidyl propionate and succinimidyl butanoate (see, e.g., Olson et al. in *Poly (ethylene glycol) Chemistry & Biological Applications*, pp 170-181, Harris & Zalipsky Eds., ACS, Washington, D.C., 1997; see also U.S. Pat. No. 5,672,662), succinimidyl succinate (See, e.g., Abuchowski et al. *Cancer Biochem. Biophys.* 7:175 (1984) and Joppich et al. *Macrolol. Chem.* 180:1381 (1979), succinimidyl ester (see, e.g., U.S. Pat. No. 4,670, 417), benzotriazole carbonate (see, e.g., U.S. Pat. No. 5,650, 234), glycidyl ether (see, e.g., Pitha et al. *Eur. J. Biochem.* 94:11 (1979), Elling et al., *Biotech. Appl. Biochem.* 13:354 (1991), oxycarbonylimidazole (see, e.g., Beauchamp, et al., *Anal. Biochem.* 131:25 (1983), Tondelli et al., *J. Controlled Release* 1:251 (1985)), p-nitrophenyl carbonate (see, e.g., Veronese, et al., *Appl. Biochem. Biotech.*, 11:141 (1985); and Sartore et al., *Appl. Biochem. Biotech.*, 27:45 (1991)), aldehyde (see, e.g., Harris et al. *J. Polym. Sci. Chem. Ed.* 22:341 (1984), U.S. Pat. No. 5,824,784, U.S. Pat. No. 5,252,714), maleimide (see, e.g., Goodson et al. *Bio/Technology* 8:343 (1990), Romani et al. in *Chemistry of Peptides and Proteins* 2:29 (1984)), and Kogan, *Synthetic Comm.* 22:2417 (1992)), orthopyridyl-disulfide (see, e.g., Woghiren, et al. *Bioconj. Chem.* 4:314 (1993)), acrylol (see, e.g., Sawhney et al., *Macromolecules*, 26:581 (1993)), vinylsulfone (see, e.g., U.S. Pat. No. 5,900,461). All of the above references are incorporated herein by reference.

In a preferred embodiment, the polymer derivatives of the invention comprise a polymer backbone having the structure:

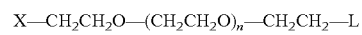

wherein:

L is the point of bonding to the nitrogen atom of the N-maleimidyl moiety;

X is a functional group as described above; and n is about 20 to about 4000.

A specific example of a homobifunctional polymer derivative comprising the above polymer backbone is shown below:

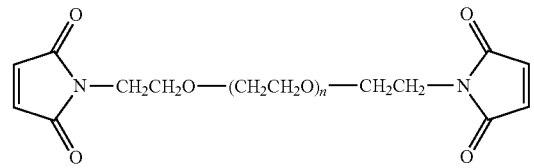

wherein n is about 20 to about 4000.

One example of a multi-armed embodiment of the invention has the following structure:

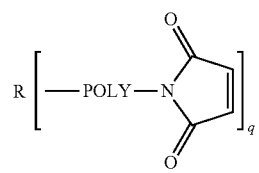

wherein:

POLY is a water-soluble and non-peptidic polymer backbone having a terminal carbon (e.g., PEG), the terminal carbon being directly bonded to the nitrogen atom of the N-maleimidyl moiety;

R is a central core molecule, such as glycerol, glycerol oligomers, pentaerythritol, sorbitol, or lysine; and q is an integer from 2 to about 300.

The derivatives of the invention can be prepared by two methods. In the first method, a water-soluble and non-peptidic polymer backbone having an average molecular weight from about 800 Da to about 100,000 Da, the polymer backbone having a first terminus bonded to a first functional group and a second terminus bonded to an amine group, is reacted with maleic anhydride to form an open ring amide carboxylic acid intermediate. The ring of the intermediate is then closed in a second step by heating the intermediate in the presence of acetic anhydride and a salt acetic acid, such as sodium or potassium acetate. Preferably, the heating step comprises heating the intermediate at a temperature of about 50° C. to about 140° C. for about 0.2 to about 5 hours. This two step process is summarized in the reaction scheme below:

Step 1

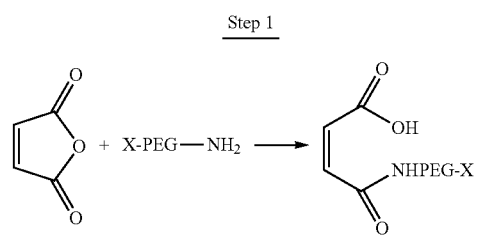

-continued

Step 2

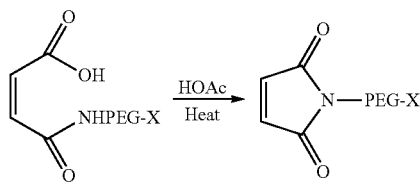

As shown, a preferred polymer backbone for use in the reaction has the formula X—PEG—NH$_2$, wherein PEG is poly(ethylene glycol) and X is a functional group which does not react with amine or maleimidyl groups. Examples of suitable functional groups include hydroxyl, protected hydroxyl, acetal, alkenyl, amine, protected amine, protected hydrazide, protected thiol, carboxylic acid, protected carboxylic acid, maleimide, dithiopyridine, and vinylpyridine. The open ring intermediate is preferably purified by precipitation prior to the heating step.

The crude N-maleimidyl polymer derivative product of the above reaction scheme may contain a substantial amount of the open ring intermediate. As a result, it is generally preferable to purify the polymer derivative product. Preferred purification techniques include precipitation and ion exchange chromatography.

In one embodiment, the purification step comprises passing the N-maleimidyl polymer derivative product through an ion exchange column, collecting an eluent containing the N-maleimidyl polymer derivative product from the column, and precipitating the N-maleimidyl polymer derivative product by contacting the product with a solvent, such as ethyl ether, isopropanol, or mixtures thereof. The precipitated product may then be collected by filtration and dried.

In a second preferred method for preparation of the N-maleimidyl polymer derivatives of the invention in a single step, an N-alkoxycarbonylmaleimide is reacted with a water-soluble and non-peptidic polymer backbone having an average molecular weight from about 800 Da to about 100,000 Da and a terminal amine group to form a N-maleimidyl polymer derivative product. An exemplary reaction scheme is shown below:

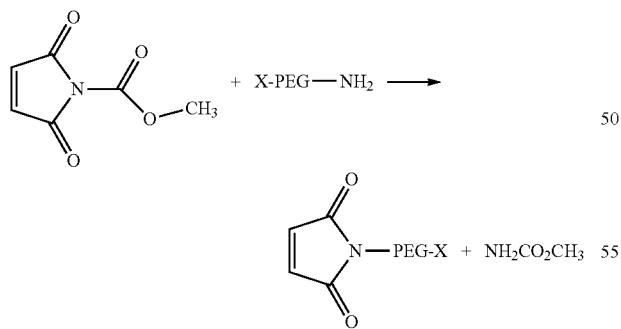

wherein PEG is poly(ethylene glycol) and X is a capping group such as alkoxy or a functional group as described above.

Purification of the crude product can also be accomplished by precipitation and ion exchange chromatography as described above.

Heterobifunctional derivatives of this invention can be prepared by the reactions described above by utilizing appropriately substituted heterobifunctional polymer amines. An example of a heterobifunctional polymer amine is a PEG amine acid:

Another example is PEG diamine, in which one of the amines is protected by a moiety such as t-Boc:

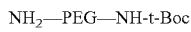

After conversion of the amine group to the maleimidyl group, the resulting N-maleimidyl PEG heterobifunctional molecule can then be converted to other useful heterobifunctional N-maleimidyl PEG derivatives. For example, a α-N-maleimidyl, ω-carboxylic acid PEG can be converted to the N-succinimidyl ester. In another example, t-Boc can be hydrolyzed to yield an ω-amino-α-N-maleimidyl PEG.

Heterobifunctional derivatives are useful when it is desired to attach different molecules to each terminus of the polymer. For example, the α-N-maleimidyl-ω-N-succinimidyl carboxylate PEG would allow the attachment of a molecule having a thiol group to the N-maleimidyl terminus of the PEG and a molecule having an amino group to the N-succinimidyl carboxylate terminus of the PEG.

The N-maleimidyl polymer derivatives of the invention can be used to react with a biologically active agent, such as a protein or peptide, to form a biologically active polymer conjugate. Since the resulting conjugate does not contain a linker between the maleimidyl moiety and the polymer terminus, there is less likelihood of degradation of the conjugate in vivo, thereby providing a more hydrolytically stable biologically active polymer conjugate.

The following examples are given to illustrate the invention, but should not be considered in limitation of the invention.

Example 1

Preparation of N-methoxy PEG$_{5000}$ maleimide

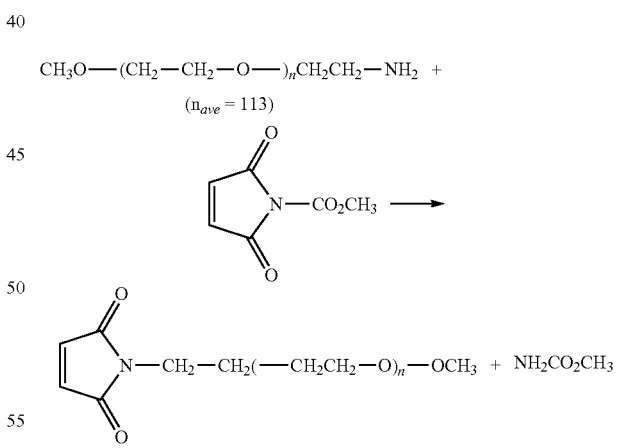

mPEG—NH$_2$ (ave. MW=5000 Da, 1 g) was dissolved in saturated aqueous NaHCO$_3$ (5 ml) and the mixture was cooled to 0° C. N-methoxycarbonylmaleimide (0.1 g) was added with vigorous stirring. After stirring for 10 minutes, water (10 ml) was added and the mixture was stirred an additional 45 minutes. The pH was adjusted to 3.0 with 0.5 N sulfuric acid and about 15 wt % NaCl was added. The reaction was extracted with CH$_2$Cl$_2$ and the combined extracts were dried over Na$_2$SO$_4$, filtered, and the filtrate was evaporated to dryness. Ethyl ether was added and the precipitate collected by filtration and dried under vacuum at room temperature overnight to yield 0.8 g of product as a white powder. The product had 79% substitution of the maleimidyl group on the PEG moiety. The $^1$H nmr was consistent with that of N-maleimidyl methoxy PEG (nmr: dmso-d6: 3.51 ppm, PEG backbone; 7.03, CH=CH).

Example 2

Preparation of N-maleimidyl poly(ethylene glycol) amine

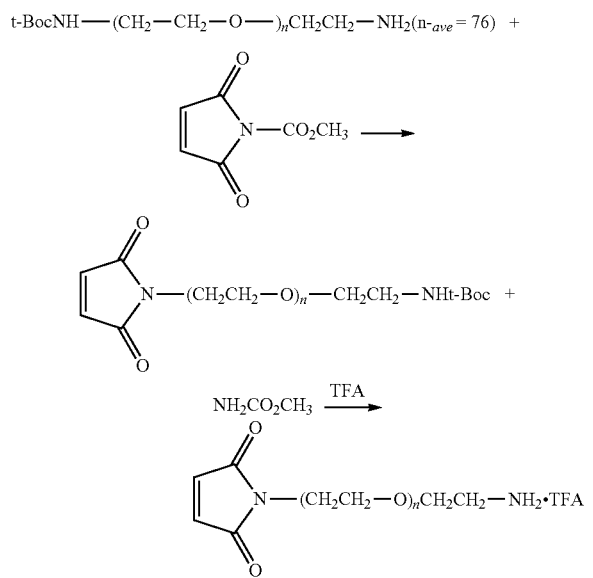

tBoc PEG amine (MW 3400 Da, 2.0 g was dissolved in saturated aqueous NaHCO$_3$ (10 ml) and the mixture was cooled to 0° C. N-methoxycarbonylmaleimide (0.28 g) was added with vigorous stirring. After stirring for 10 minutes, water (20 ml) was added and the mixture was stirred for an additional 45 minutes. The pH was adjusted to 3.0 with 0.5 N sulfuric acid and about 15 wt % NaCl was added. The reaction was extracted with CH$_2$Cl$_2$ and the combined extracts were dried over Na$_2$SO$_4$, filtered, and the filtrate was evaporated to dryness. Ethyl ether (150 ml) was added and the precipitate collected by filtration and dried under vacuum at room temperature overnight to yield 1.5 g of the product as a white powder. The product had 74% substitution of the maleimidyl group on the PEG moiety. The $^1$H nmr was consistent with that of N-maleimidyl methoxy PEG (nmr: dmso-d6: 3.51 ppm, PEG backbone; 7.03, HC=CH).

The above described crude N-maleimidyl PEG t-Boc amine was purified by ion exchange chromatography. The crude product (1.45 g in 100 ml deionized water) was loaded onto DEAE Sepaharose, 100 ml) and eluted with aqueous NaCl (15%, pH 3). The eluent was extracted with CH$_2$Cl$_2$ (3×100 ml) and the extract was dried over Na$_2$SO$_4$, evaporated to dryness and precipitated with ethyl ether (100 ml). The precipitate was collected by filtration and dried under vacuum at room temperature to yield 0.7 g of N-maleimidyl PEG t-Boc amine. The $^1$H nmr was consistent with that of N-maleimidyl PEG t-Boc amine CH nmr: dmso-d6: 1.37 ppm, t-butyl; 3.51, PEG backbone; 7.03, HC=CH).

N-maleimidyl PEG t-Boc amine (0.7 g) was dissolved in trifluoroacetic acid/CH$_2$Cl$_2$ (1:1, 20 ml) and stirred at room temperature for 1 h. The solution was evaporated to dryness under vacuum and the product was precipitated by the addition of ether (100 ml). The product was dried under vacuum overnight to yield 0.58 g of N-maleimidyl PEG ammonium trifluoroacetate as a white powder. The product had 92% substitution of the N-maleimidyl group on PEG by GPC. The product was shown by $^1$H nmr to have about 100% substitution of the amine group on PEG and about 90% of the maleimidyl group on PEG. $^1$H nmr (dmso d-6): 3.51 ppm, PEG backbone; 7.03, HC=CH, 7.80, NH$_3^+$

Example 3

Preparation of N-maleimidyl poly(ethylene glycol) propionic acid and N-maleimidyl poly(ethylene glycol) N-succinimidyl propionate

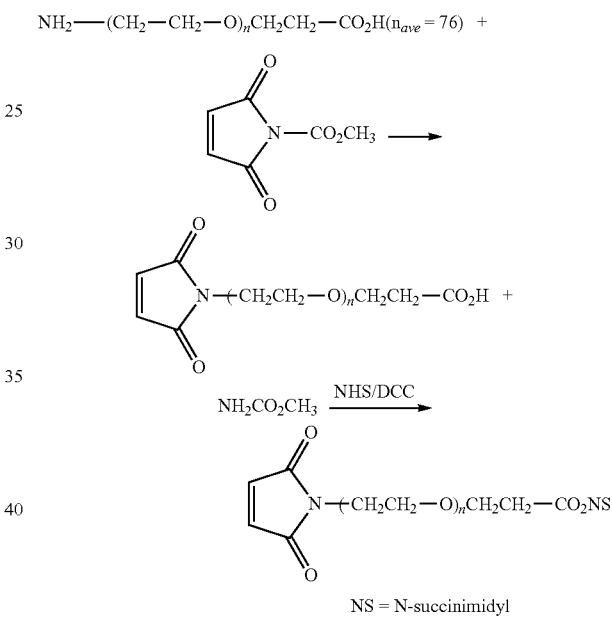

NS = N-succinimidyl

NH$_2$—PEG—O—CH$_2$CH$_2$CO$_2$H (MW 3400 Da, 2.0 g) was dissolved in a saturated aqueous solution of NaHCO$_3$ (10 ml) and the mixture was cooled to 0° C. Powdered N-methoxycarbonylmaleimide (0.28 g, 3 eg.) was added with vigorous stirring. After stirring an addition 10 min., 20 ml of H$_2$O was added and the mixture was stirred for 45 min. at room temperature. The pH was adjusted to 3 with 0.5 N H$_2$SO$_4$ and NaCl was added to a concentration of about 15 wt %. The reaction mixture was extracted with CH$_2$Cl$_2$ (100 ml×3), dried over Na$_2$SO$_4$ and evaporated to dryness. After precipitation with ether (150 ml), the product was collected by filtration and dried under vacuum (yield: 1.8 g). Purity was 95% by GPC. $^1$H nmr (dmso-d6): 2.44 ppm, t, CH$_2$CO$_2$—; 3.27, t, CH$_2$—N; 3.51, br s, PEG backbone); 7.03, HC=CH.

N-maleimidyl-PEG—OCH$_2$CH$_2$CO$_2$H (1.0 g) was dissolved in CH$_2$Cl$_2$ (15 ml) and N-hydroxysuccinimide (0.042 g, 2 eq.) and DCC (0.074 g, 2 eq.) was added and the solution was stirred overnight at room temperature. The resulting mixture was concentrated under vacuum and the product precipitated by addition of IPA:ether (1:1, 100 ml). The product was washed with ether (30 ml) and dried under vacuum overnight (yield: 0.89 g). $^1$H nmr (dmso-d6): 2.81 ppm, s, —$CH_2CH_2$— on NS; 2.93, t, $CH_2$—$CO_2$; 3.51, PEG backbone, br s; 7.03, HC=CH.

Example 4

Preparation of 4-Arm 10 KDa PEG maleimide

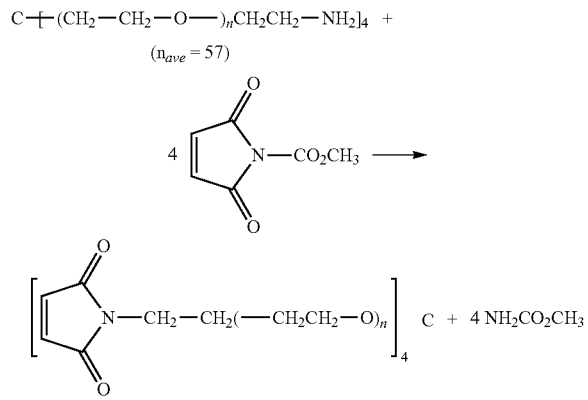

4-Arm PEG amine (ave. MW=10,000 Da, 1 g) was dissolved in saturated aqueous $NaHCO_3$ (5 ml) and the mixture was cooled to 0° C. N-methoxycarbonylmaleimide (0.2 g) was added with vigorous stirring. After stirring for 10 minutes, water (10 ml) was added and the mixture was stirred an additional 45 minutes. The pH was adjusted to 3.0 with 0.5 N sulfuric acid and about 15 wt % NaCl was added. The reaction was extracted with $CH_2Cl_2$ and the combined extracts were dried over $Na_2SO_4$, filtered, and the filtrate was evaporated to dryness. Ethyl ether was added and the precipitate collected by filtration and dried under vacuum at room temperature overnight to yield 0.8 g of the product as a white powder. The product had 85% substitution of the maleimidyl group on the PEG moiety. The $^1$H nmr was consistent with that of N-maleimidyl 4-arm PEG (nmr: dmso-d6: 3.51 ppm, PEG backbone; 7.03, CH=CH).

Many modifications and other embodiments of the invention will come to mind to one skilled in the art to which this invention pertains having the benefit of teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A multi-functional N-maleimidyl polymer derivative having the formula:

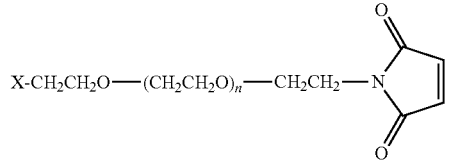

wherein:
X is carboxylic acid; and
n is about 20 to about 4000.

* * * * *